United States Patent [19]

Peter et al.

[11] 4,345,976
[45] Aug. 24, 1982

[54] PROCESS FOR SEPARATING MIXTURES OF SUBSTANCES OF LOW VOLATILITY

[75] Inventors: Siegfried Peter, Lange Zeile 138, D-8520 Erlangen, Fed. Rep. of Germany; Gerd Brunner, Roth; Rolf Riha, Friedelsheim, both of Fed. Rep. of Germany

[73] Assignee: Siegfried Peter, Uttenreuth-Weihr, Fed. Rep. of Germany

[21] Appl. No.: 10,143

[22] Filed: Feb. 7, 1979

Related U.S. Application Data

[63] Continuation-in-part of Ser. No. 739,325, Nov. 5, 1976, abandoned, which is a continuation of Ser. No. 632,087, Nov. 14, 1975, abandoned, which is a continuation of Ser. No. 496,871, Aug. 12, 1974, abandoned.

[30] Foreign Application Priority Data

Aug. 10, 1973 [DE] Fed. Rep. of Germany ....... 2340566

[51] Int. Cl.³ .......................... B01D 3/36; C11C 1/10
[52] U.S. Cl. ..................................... 203/49; 203/58; 203/60; 203/62; 203/63; 203/67; 203/68; 203/69; 203/70; 203/75; 203/87; 203/96; 208/348; 208/356; 208/357; 260/419; 260/428; 568/869
[58] Field of Search ................. 203/49, 69, 87, 50–68, 203/70, 6–9, 76, 79, 38, 29, 91, 96, 74, 75; 260/419, 428; 568/869; 208/348, 356, 357, 358

[56] References Cited

U.S. PATENT DOCUMENTS

| | | | |
|---|---|---|---|
| 1,439,685 | 12/1922 | Bodman | 203/49 |
| 1,965,566 | 7/1934 | Beck et al. | 260/419 |
| 2,351,249 | 6/1944 | Ziegler et al. | 260/419 |
| 2,838,480 | 6/1958 | Swern et al. | 260/419 |
| 3,378,467 | 4/1968 | Colton et al. | 203/49 |
| 3,806,619 | 4/1974 | Zosel | 203/49 |
| 3,969,196 | 7/1976 | Zosel | 203/49 |

Primary Examiner—Wilbur L. Bascomb, Jr.
Attorney, Agent, or Firm—Wyatt, Gerber, Shoup, Scobey & Badie

[57] ABSTRACT

The invention involves a process for substantially separating the components of mixtures of substances at least one of which is of low volatility while the other is of low or no volatility, the process using a compressed gas under supercritical conditions and an entrainer which increases the concentration of said mixture in the gaseous phase as well as the separation factor between the components to be separated. The process operates in two distillation zones the first of which substantially separates the components of low volatility in a process similar to a rectification process while the second distillation zone separates the top product of the first distillation zone from the gas with the aid of the entrainer which is condensed partially and in this state is passed in countercurrent to the gas carrying the separated component of low volatility.

16 Claims, 5 Drawing Figures

Fig. 1  $K_1, K_2, K_3$, critical points of the binary system at temperatures $T_1, T_2, T_3$. $X_A$ composition of the liquid phase, $X_B$ composition of the gaseous phase at Temperature $T_2$ and at working pressure.

Fig. 2 Phase equilibria of type I

Fig. 3 Phase equilibria of type II

PROCESS FOR SEPARATING MIXTURES OF SUBSTANCES OF LOW VOLATILITY

This application is a continuation-in-part of U.S. Application Ser. No. 739,325 filed Nov. 5, 1976, which in turn is a continuation of U.S. Application Ser. No. 632,087 filed Nov. 14, 1975, this application which in turn being a contimation of U.S. Application Ser. No. 496,871 filed Aug. 12, 1974, all these prior applications being now abandoned.

BACKGROUND OF THE INVENTION

In the technology of thermal separation, the separation of mixtures of substances of low volatility and high sensitivity to temperatures, frequently poses a difficult problem. The processes of vacuum distillation and molecular distillation were designed to overcome this problem, but these methods fail if azeotropic mixtures are formed, or if the separation factors are very low, the separation factor being the ratio of the distribution coefficients of two substances between the gaseous phase and the liquid phase. Extraction processes are equally unsatisfactory in these cases, particularly if the separation of the extracted substance from the extraction agent—a necessity once the extraction process has been completed—involves thermal burden which is excessively high.

The present invention relates to a process for separating substances of very low volatility, one of which may even be not volatile at all, present in the form of mixtures, from one another by extractive distillation at low temperature. The barely volatile substances are rendered evaporable at low temperatures, with the aid of a gaseous agent under pressures exceeding or equalling its critical pressure, such gaseous agents, because of the supercritical conditions under which they are employed, hereinafter being referred to as "supercritical" agents.

It is well known that supercritical substances under high pressure, have properties which in many respects are similar to those of a liquid. In the state of equilibrium, the concentration of a barely volatile substance in the gaseous phase under pressure, may be higher by many powers of ten than would be expected from its vapor pressure. This effect is partly due to the solubilizing properties of the gaseous phase, and partly to the dissolution of the supercritical gaseous agent in the mixture of barely volatile substances.

In this way it is possible to obtain a distribution of the substances to be separated between a liquid and a gaseous phase, of sufficiently different density.

Suggestions to make use of this effect have been made in the past; cf. U.S. Pat. No. 2,420,185 to Messmore (Philips Petroleum Co.); T. P. Zhuze and A. A. Kapelyushnikov, U.S.S.R. Pat. No. 113,325; and U.S. Pat. No. 3,969,196 to Zosel (Studiengesellschaft Kohle m.b.H.).

On principle, it should be possible to carry out a separation process merely with the aid of the equilibrium between the gaseous and liquid phases. It is usually found, however, that the separation factors between the barely volatile substances to be separated, are not sufficiently modified by the supercritical agent.

Moreover, it is of decisive importance for the economics of a separation process that no compression work should be necessary on the circulating gaseous phase, However, the gas conducted in a cycle must be largely freed from the barely volatile substances before it reenters the principal distillation zone because remixing would impair the quality of the products. Heating of the gaseous phase in order to achieve a sufficient reduction of the content of barely volatile substances, is out of the question, because the temperatures required for this process would frequently result in an excessively high thermal burden on the substances.

The problem of the present invention, therefore, is to provide a process wherein, on the one hand, the distribution ratio of the barely volatile substances to be separated in the gaseous phase and in the liquid phase is improved so that the best possible separation is obtained, and, on the other hand, it is possible to free the gaseous phase conducted in a cycle, from the entrained barely volatile substances, without the necessity of a pressure release or a substantial temperature rise. Manifestly, the problem of the invention has several aspects (improvement of the acceptance of the barely volatile substances by the recycled gaseous phase; freeing the gas from these substances absent any substantial pressure release or temperature increase). In cases in which the pressures are about 1 to 2 times of that the critical pressure of the compressed supercritical gas and the temperatures are a little bit higher (up to about 100° C.) than the critical temperature of the compressed supercritical gas, a rise of temperature the absence of an entrainer may lead to a partial separation of the barely volatile substance dissolved in the compressed gas, as mentioned in U.S. Pat. No. 3,969,196. This separation concerns only part of the dissolved barely volatile substance (about 30 to 60 percent by weight depending on the temperature raise), so that the recycling of the so treated cycle gas into the sump of the first distillation zone leads to so much remixing, that the intended substance separation will be impossible. Partial condensation of the entrainer in a second distillation zone accompanied with the "wash" of the cycle gas in countercurrent according to this invention leads to improved separation of the barely volatile components dissolved in the cycle gas residue is less than 0.2 percent by weight of the originally dissolved components), so that the recycling of the cycle gas into the sump of the first distillation zone will not lead to a disadvantageous remixture. While the former aspect has been recognized by the above-noted U.S. Pat. No. 3,969,196 which has attempted to solve that part of the problem in a manner distinct from the present approach, the latter aspect has not been dealt with in the prior patent which proposes precisely that pressure release or temperature rise whose elimination is one of the primary objectives of the present invention.

BRIEF SUMMARY OF THE INVENTION

In the description of the invention which follows, reference will be had to the accompanying drawings wherein.

The invention involves a process for separating the components of mixtures of substances of low volatility, one of which may even be of no volatility, by using a compressed gas under supercritical conditions, and an entrainer designed to increase the concentration of said mixtures of barely volatile substances in the gaseous phase as well as the separation factor between the components to be separated.

The process calls for two distinct distillation zones. The compressed gas is recycled through these distillation zones. In the first of these zones, the mixture of barely volatile substances and the entrainer is contacted by the compressed gas under supercritical conditions, and process conditions are so selected that one of the barely volatile substances, mixed with some of the entrainer, will be separated from the other barely volatile component and the compressed gas and will pass to the bottom of the first distillation zone, while the other component and the remainder of the entrainer are carried along by the cycle gas to the top of the first distillation zone. This top product of the first distillation zone is then passed to a second distillation zone where the other barely volatile component is separated from the cycle gas, and the entrainer is condensed partially to pass in countercurrent to the cycle gas as to "wash" it free of remnants of the barely volatile mixture.

The bottom product of the second distillation zone is divided, and a part is returned to the top of the first distillation zone for reflux: the top product of the second distillation zone is substantively uncontaminated cycle gas which is recycled to the bottom of the first distillation zone.

The components of the mixture of barely volatile substances, one of which may even be not volatile at all, are recovered, in combination with some of the entrainer, at the bottom of the first and second distillation zone, respectively. They are separated from the entrainer in any manner known in the art, such as simple or vacuum distillation, or by stripping or extraction.

DETAILED DESCRIPTION OF THE INVENTION

Before proceeding to a description of the invention in greater detail, it appears expedient to clearly define the agents and the substances to be separated, and to provide a brief explanation of the thermodynamic principles on which their interaction is based.

Gases suitable for beng used in the form of a compressed supercritical gas, for taking up the barely volatile substances, are defined by their compliance with the requirement that their critical temperature is lower than the temperature at which the separation of the barely volatile substances is to be carried out. Gases having a relatively low critical pressure (e.g. about 30–50 atm; this group inclues e.g. hydrocarbons, halogenated hydrocarbons, alkylamines, ether etc.) are preferred, generally speaking, to gases having higher critical pressures (above 50 atm; this group includes $CO_2$, $P_{cr}=73$ atm., ammonia $P_{cr}=111$ atm, sulfur dioxide, $P_{cr}=77.7$ atm., $N_2O$, $P_{cr}=71.6$ atm. etc.). In special cases, however, e.g. on grounds of safety or because of a particular specific interaction between the gas present in a supercritical state, and the barely volatile substance(s) to be separated, gases having a high critical pressure may also be used as the supercritical agent.

At the critical point, defined by the critical temperature $T_{cr}$ and the critical pressure $P_{cr}$, the liquid and the gaseous phases of a substance have the same densitiy. In the dissolution of barely volatile substances in compressed gases, the density of the gas is the characteristic factor. The closer the density of the gas approaches the density of the liquid, the better the compressed gas is able to dissolve the barely volatile substances. The lower the critical pressure of the gaseous agent, the lower is the pressure required for compressing the supercritical gas to a density which approaches or exceeds the density of the liquid. Experience has demonstrated that with equal density under supercritical conditions, generally speaking, the solubility in the supercritical gaseous agent is materially enhanced compared with that in the liquid state.

The choice of the supercritical gas is limited only by the requirement that its critical temperature is lower than the temperature at which the separation process is to be carried out. This working temperature, in turn, is limited by the requirement that the barely volatile substances must not be exposed, in the course of the separation procedure, to any thermal decomposition. With most complex organic compounds, because of their sensitivity, the upper temperature limit is in the range of from 120° to 180° C. With compounds not very sensitive to temperature, such as hydrocarbons, working temperatures up to 400° C. may be employed. In these cases, compounds such as toluene ($T_{cr}=320.6°$ C.) may be used as the supercritical compressed gas.

Figure 1:
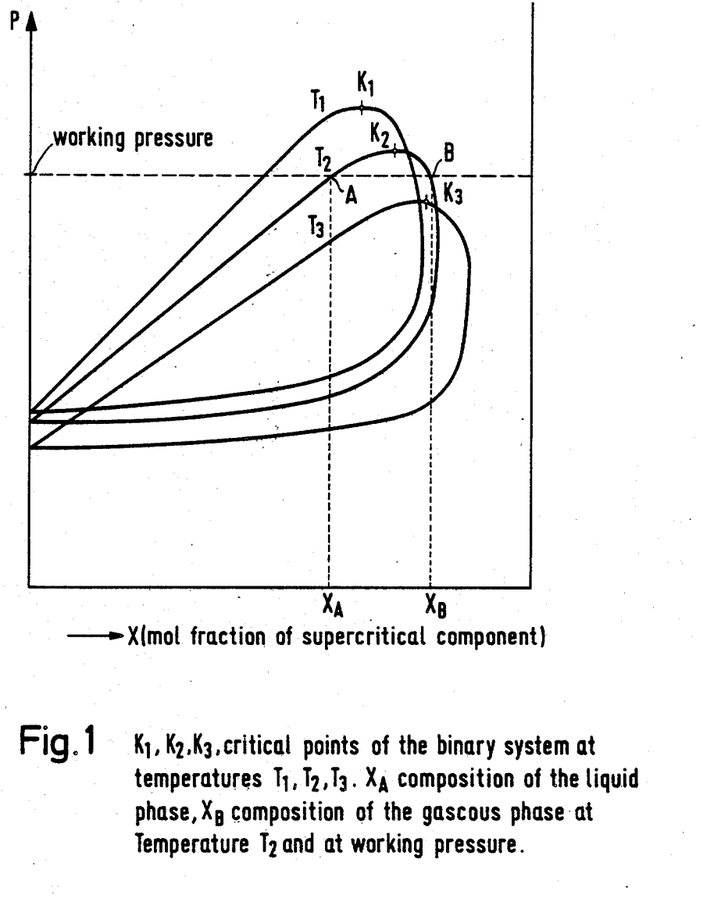
FIG. 1 illustrates phase boundary lines in a binary system at different temperatures.
Figure 2:
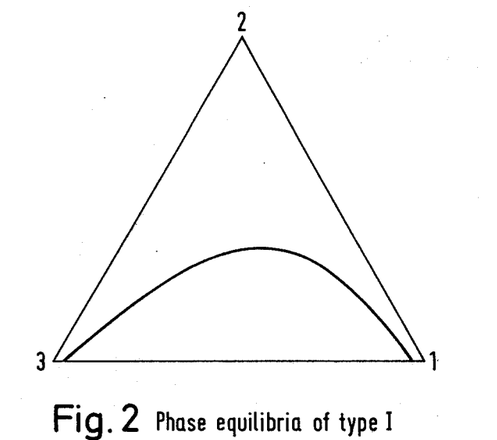
FIG. 2 shows a type I phase equilibrium in a binary system.
Figure 3:
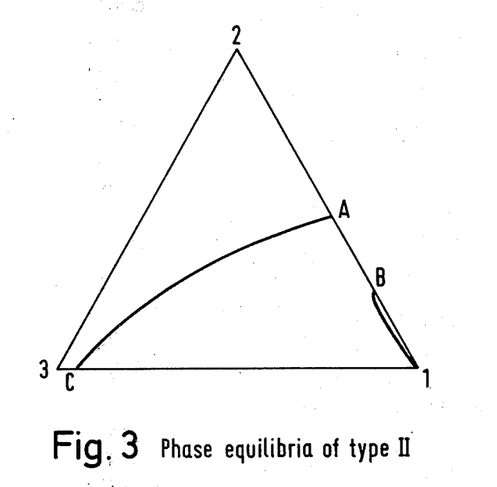
FIG. 3 shows a type II phase equilibrium in a ternary system.

Suitable entrainers are compounds which in the binary system with the supercritical gaseous agent, in the temperature range between the critical temperature of the gaseous agent and the highest temperature admissible for the barely volatile substances, at pressures ranging from 60 to 300 atm., display a closed loop of the phase boundary line, cf. FIG. 1. Inasmuch as the loop of the phase boundary line changes with the temperature, a change in temperature, at a given pressure, can cause the loop of the phase boundary line to intersect the pressure ordinate, as at $T_1$ and $T_2$, or else the loop of the phase boundary line is disposed below the working pressure, as at $T_3$ in FIG. 1. In the latter case the binary system of entrainer and supercritical agent, at the working pressure, is supercritical, i.e. it is no longer possible to distinguish between the liquid and the gaseous phases. In the pseudo-ternary system of supercritical compressed gas, entrainer and mixture of barely volatile substances, the behavior just described of the binary system of supercritical gaseous agent and entrainer, at constant pressure, has the following consequences: At the temperature $T_3$, at which the binary system gas/entrainer is supercritical, there is present in the ternary system: gas(1)/entrainer(2)/barely volatile substances(3), a phase equilibrium of type I according to Treybal, "Liquid Extraction", 2nd ed., McGraw-Hill, New York 1963, which has a closed phase boundary line, as shown in FIG. 2. If, however, temperature and pressure are so chosen that at the working pressure, the binary system gas/entrainer has a miscibility gap (temperatures $T_1$ and $T_2$ in FIG. 1), there exists in the ternary system a phase equilibrium of the type II according to Treybal (cited above) which has discontinuous phase boundary line (FIG. 3). The phase boundary line for the gaseous-phase extends from B to the gas corner; the phase boundary line for the liquid phase extends from A to C.

As described below in greater detail, the separation process of this invention uses in the first distillation zone, conditions involving a phase equilibrium of type I, for the reason that this increases the load taken up by the gaseous phase. In the second distillation zone wherein the cycle gas is freed from barely volatile substances, conditions are employed which create a phase equilibrium of type II. The conditions are so chosen that in the transition from a phase equilibrium of type I to one of type II, entrainer condenses and passes in countercurrent to the cycle gas whereby to free the same from barely volatile substances.

The barely volatile substances in the mixtures to be separated in accordance with the invention, preferably are organic compounds, but may also be metalorganic compounds, esters of inorganic acids, or inorganic compounds. At high pressures, even inorganic compounds are soluble in supercritical agents such as ammonia, carbon dioxide and supercritical water vapor. Cf. the solubility of NaCl in supercritical water vapor, and of iodine in supercritical $CO_2$. The invention even extends to mixtures wherein one of the components is not volatile at all. Details and examples of supercritical gases, entrainers and barely volatile substances to be separated, as well as working examples of the present process, will be provided below, following a description of the separation process of the invention with reference to FIGS. 4 and 5 of the drawings which diagrammatically illustrate two embodiments of apparatus used in carrying out the invention.

Figure 4:
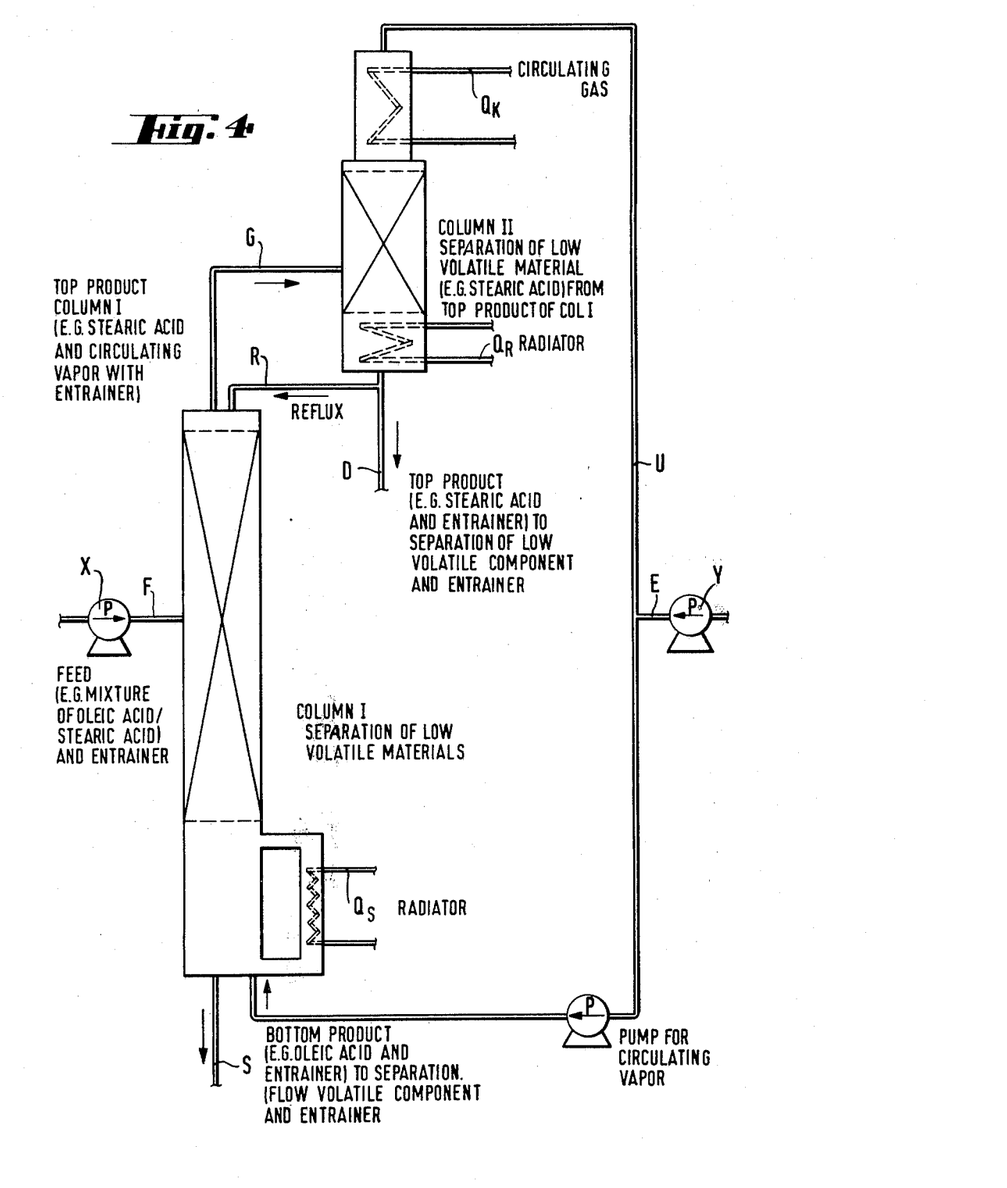
FIG. 4 illustrates diagrammatically apparatus for carrying out the separation process of the invention.

Referring first to FIG. 4, this shows a distillation column I. Approximately in the middle of this column a feed conduit F is disposed, while at the bottom of this column, a discharge conduit S is arranged. Above the sump of column I and the terminal of discharge conduit S, a radiator $Q_s$ is disposed. At the top of column I, a conduit G leads to a column II, terminating at a point not higher, and preferably below the horizontal center line of column II. At the bottom of column II, a conduit is arranged which divides into two branches, a return conduit R leading back to the top of the column I, and a discharge conduit D. At the bottom of the column II, a radiator $Q_R$ is disposed, while the top of this column mounts a condenser $Q_K$. A circulating gas conduit extends from the pump P to the sump of column I, includes the conduit G between the two columns, and extends from the top of column II, via a portion U, back to the point P. Other pumps, X and Y, are provided in feed conduit F and gas conduit E, for feeding and loss compensation for entrainer and circulating gas, respectively.

Plate columns and packed columns such as are commonly used in separation technology are suitable for carrying out the extractive distillation process of the present invention. The only requirement is that the walls of the columns, the pipelines and the heat exchangers must withstand the pressures and temperatures prevailing during the process.

In the operation of the separation process of the invention in the apparatus of FIG. 4, the mixture of barely volatile substances to be separated, admixed with the entrainer at a predetermined rate of admixture, is introduced, through conduit F, into the column I. As will be explained below in greater detail, conditions in this column are so chosen that the mixture of barely volatile substances and entrainer, on being contacted by the circulating gas at high pressure and under supercritical conditions, under the influence of the entrainer which increases the concentration of the barely volatile substances in the compressed gas while at the same time increasing the separation factor between the barely volatile substances, will substantially be separated and divided into two portions, one travelling downward and containing, besides entrainer, one of the barely volatile components of the mixture to be separated while the other travels upward to be taken along by the circulating gas to the top of column I. In this operation, radiator $Q_s$ provided at the bottom of column I serves as a circulating evaporator which supplies the heat quantity necessary for heating the circulating material and for evaporation.

The top product of column I which in addition to the circulating compressed gas, contains, besides the remainder of the entrainer, the other one of the barely volatile components of the mixture to be separated, passes through conduit G, to the column II for upward travel therein. When the complex:gas, second barely volatile component, entrainer, enters the zone of the condenser $Q_K$, the entrainer is condensed by removal or addition of the necessary heat quantity and will travel downward, in counter-current to the rising circulating gas, and will take along the second barely volatile component, thus substantially freeing the circulating gas from said component; the barely volatile component and entrainer will collect at the bottom of the column II while the circulating gas, substantially freed from barely volatile substances, will pass from the top of column II, via conduit u and pump P, to the bottom of column I.

The product withdrawn from the the sump of column II is divided; one portion is recovered, as distillation product, through conduit D while the other is returned, through conduit R, to the top of column I, for reflux. Radiatior $Q_R$ provided at the bottom of column II is designed to heat the mixture of the barely volatile substance and entrainer collected at the bottom of column II, to approximately the temperature prevailing at the top of column I.

The sump product discharged through conduit S from the column i, and the top product of column I discharged, following the cleansing operations in column II, through conduit D at the bottom of column II, contain, substantially, one or the other of the barely volatile components, and a certain quantity of entrainer and dissolved gas.

The entrainer is selected to boil at a temperature at which the barely volatile substances to be separated are still stable, because the entrainer is preferably separated from the barely volatile substances recovered at S and D by a simple distillation. However, in some cases it may be advantageous to carry out this operation in a vacuum, or to achieve the most complete separation of the entrainer from the barely volatile substances by stripping or extraction. This separation may be performed in any manner well known in the art and therefore, no instrumentality for carrying it out has been included in the drawings. In some instances, indeed, it may not even be desired to separate the entrainer from the barely volatile substances which may be worked up further, advantageously, with the entrainer still being present.

Figure 5:
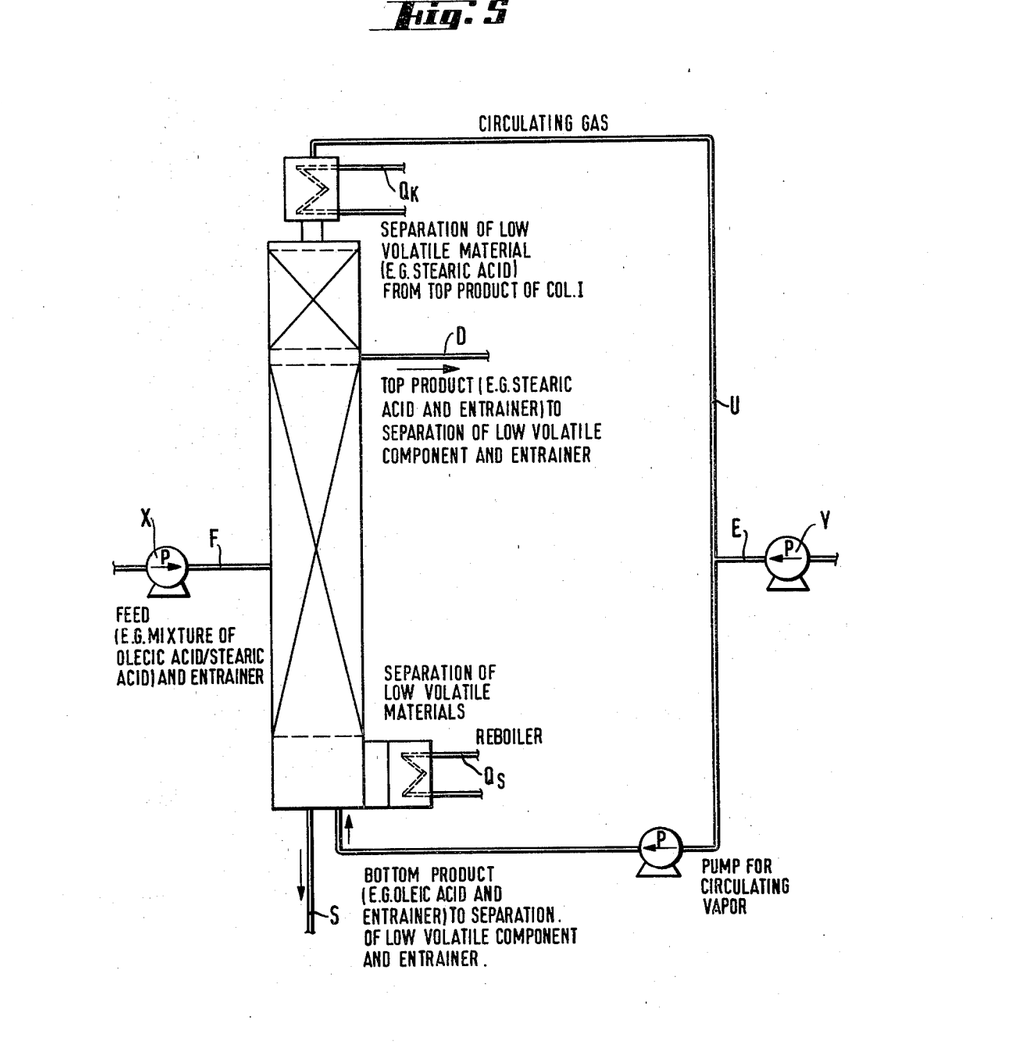
FIG. 5 illustrates diagramatically, a modification of the apparatus of FIG. 4.

Another embodiment of the apparatus which may be used in carrying out the separation process of the invention is illustrated, diagrammatically, in FIG. 5. This apparatus corresponds in all respects to that shown in FIG. 4, except that column II, instead of being a separate column disposed in proximity to column I, constitutes the upper part of a suitably extended rectifying column the lower part of which corresponds to column I in FIG. 4. The only other difference in FIG. 5 is that discharge conduit D, instead of extending downward from the bottom of column II, extends sideways from an appropriate point of column II. It is expedient to provide heat exchanging means (not shown in the drawing) at the point where discharge conduit D leads away from column II. Conduits G and R (not shown in the drawing) are provided in the apparatus of FIG. 5 the same as in that of FIG. 4.

Besides the components of barely volatile material, the product streams contain entrainer and supercritical components. The latter are present in a concentration corresponding to the solution equilibrium at the temperatures and pressures concerned. The proportion of supercritical components dissolved in the products may be separated by a pressure release and, if desired, returned to the cycle; however, the proportion of supercritical components dissolved in the products is negligible in relation to the volume of the cycle. If a pressure release and corresponding very minor recompression become necessary, pressure gates are resorted to in a manner well known in the art. The process of the present invention thus makes it possible to rectify high-boiling, temperature-sensitive substance mixtures under high pressures of the supercritical components without having to carry out compression operations to any appreciable extent.

As noted above, the material to be separated is conducted, together with the entrainer, to the column I through intake F. The amount of entrainer is so proportioned that the loss of entrainer incurred during the separation process is compensated for.

When the circulating gas is to be freed from the barely volatile substances by the entrainer in a rectifying operation, care should be taken in choosing the entrainer so that the mixture of entrainer and supercritical gas is subcritical at prevailing temperatures and pressures. It is well known that the critical pressure of a mixture consisting of a supercritical and a subcritical component decreases with decreasing differences between the temperature of the system and the critical temperature of the subcritical component. On the one hand, the entrainers according to the present invention should be readily separable from the components of low vapor pressure but, on the other hand, their critical temperature and hence their boiling point should not be too low so that the critical pressure of the system of entrainer and supercritical components is higher than is the working pressure at the working temperature.

For example, the combination of supercritical propane with subcritical butane may not be a suitable system because the binary system is supercritical at a pressure required in order to sufficiently increase the concentration of the substances of low vapor pressure in the gaseous phase. Consequently, it would not be possible in this case to separate the substances of low vapor pressure from the circulating gaseous phase with the aid of the entrainer. The choice of supercritical agents to be used in a specific case depends on the type of mixture of barely volatile substances to be separated and on the conditions of temperature and pressure prevailing during the separation. Examples of supercritical agents to be used according to the invention are aliphatic hydrocarbons and halogen containing aliphatic hydrocarbons containing from 1 to 4 carbon atoms such as ethane and/or propane. The preferred halogens are fluorine, chlorine and bromine. Supercritical agents which are preferred according to the invention, include inter alia, methane, ethane, propane, trifluoro-chloromethane, difluoro-dichloromethane, trifluoro-bromomethane and/or methyl fluoride. However, it is also possible according to the invention to use inorganic materials as supercritical agents, for example, carbon dioxide and ammonia, the first-mentioned agent being preferred.

Supercritical gaseous agents suitable for purposes of the invention are exemplified by the following list giving their critical temperature $T_c$:

|  | $T_c$, 0° C. |
| --- | --- |
| 1,1-difluoroethylene | 29.7 |
| methane | −82.5 |
| carbon monoxide | −140.0 |
| propylene | 91.8 |
| 1,1-trifluoroethane | 73.1 |
| vinylfluoride | 54.7 |
| monobromotrifluoromethane | 66.8 |
| monochlorodifluoromethane | 96.2 |
| chloropentafluoroethane | 80.0 |
| monochlorotrifluoromethane | 28.8 |
| carbon dioxide | 31.0 |
| $SF_6$ | 45.6 |
| tetrafluoromethane | −45.7 |
| trifluoromethane | 26.0 |
| ammonia | 132.4 |
| hydrogen | −239.97 |
| hydrogen bromide | 90.0 |
| hydrogen chloride | 51.4 |
| nitrogen | −147.1 |
| nitrous oxide | 36.5 |
| oxygen | −118.8 |
| sulfur dioxide | 157.2 |
| ethane | 35.0 |
| ethylene | 9.5 |
| propane | 96.8 |
| i-butane | 133.7 |
| difluorodichloromethane | 11.5 |
| methyl chloride | 143.1 |
| $C_2F_4Cl_2$ | 145.7 |
| helium | −268.0 |
| neon | −228.6 |
| hydrogen sulfide | 100.5 |
| argon | −122.4 |
| krypton | −63.7 |
| xenon | 16.8 |
| radon | 104.5 |
| n-butane about | 152 |
| $CH_3F$ | 44.9 |
| hydrogen iodide | 150.8 |
| methylamine | 157 |
| methylether | 127 |

In general, the concentration of the entrainer in the gas phase is increased by a factor of between 1 and 4, compared with the vapor pressure.

The process of the invention may be used for the separation of a wide variety of mixtures. For example, it can be used for separating substances differing only by the number of double bonds present in the molecule, i.e. one or more olefinic bonds. The separation of a mixture of oleic acid and stearic acid in the presence of a supercritical agent under high pressure is an example of a successful application of the process of the invention. The vapor pressures of the two fatty acids are very low and do not differ from one another appreciably. At temperatures above 180° C. the saturation pressures only reach values of about 3 mm Hg. Oleic acid is no longer stable at these temperatures. Mixtures wherein only one substance is barely volatile while the other is not volatile at all, include mixtures of mineral oils and clay particles.

Suitable entrainers which influence the relative volatility or the separation factor of the two components are, for example, benzene; toluene; xylene; furan and its derivates such as 2-methyl-furan, furfural, furan-3-aldehyde and ethyl-furan; acetonitrile; methylene chloride; acetone; and hydrocarbons with a sufficiently high critical temperature and a boiling temperature below 200° C., such as e.g. hexane, cyclohexane, methyl cyclohexane, n-heptane, iso-heptane, n-octane, iso-octane, nonane, decane, etc. The separation factor for a mixture of oleic acid and stearic acid is normally in the vicinity of 1. By adding benzene to a mixture of oleic acid and stearic acid in the proportion of 1:1 with ethylene at about 160 atm. (160 bar) and 102° C. the separation factor is increased from 0.93 to 1.5 if the benzene concentration, based on the fatty acids (i.e. disregarding the supercritical component) amounts to 75 mol percent. The separation factor is defined as the ratio $K_{stearic\ acid}/K_{oleic\ acid}$. For the entrainers acetone, methylene chloride, n-heptane, iso-octane, acetonitrile, 2-methylfuran, the most advantageous concentration ranges from 5 to 25 percent by weight, based on the mixture of fatty acids and entrainers. The most advantageous concentration for benzene is from 5 to 70 percent by weight, based on the mixture of fatty acids and entrainers.

The concentration of the fatty acids in the gas phase is increased at a pressure of about 160 atm. (160 bar) and 102° C. by the factor $5 \times 10^3$, compared with the vapor pressure, when the gaseous phase is ethylene. The addition of an entrainer such as benzene, acetone or another compound in accordance with this invention leads to a further increase of the concentration of the fatty acids in the gas phase, approximately by the factor 10. This additional increase of the concentration is desirable but it is not essential to the process. It could also be brought about by increasing the pressure.

As further examples of the application of the process according to the invention there may be mentioned the separation of a mixture of mono-, di-and tri-glycerides and the separation of a mixture of polyhydric alcohols. Suitable entrainers for these separation problems are alcohols containing up to 7 carbon atoms, ketones containing up to 5 carbon atoms, and water. Suitable entrainers from these classes of substances are, for example, methanol, ethanol, n-propanol, iso-propanol, n-butanol, iso-butanol, acetone, methyl ethyl ketone, ethyl ethyl ketone. The concentration of the polyhydric alcohols in the gaseous phase is increasing at a total pressure of about 200 atm. (200 bar) by a factor of $10^3$ to $10^5$, compared with the vapor pressure; this effect is only slightly influenced by the supercritical agent used. The condditions are analogous for glycerides.

More generally speaking, entrainers suitable for purposes of the present separation process may be exampli­fied by the following list giving the boiling temperatures $t_b$.

|  | $t_b$,°C. |  | $t_b$,°C. |
|---|---|---|---|
| water | 100 | trichloroethylene | 86.9 |
| n-hexane | 68,8 | nitromethane | 101.2 |
| cyclohexane | 80,8 | carbon disulfide | 46.3 |
| benzene | 80,2 | butane | 0.5 |
| toluene | 110,8 | acetaldehyde | 20.2 |
| methanol | 64,4 | acetonitrile | 81.6 |
| ethanol | 78,4 | ethylamine | 16.6 |
| n-propanol | 97,2 | allyl alcohol | 96.6 |
| i-propanol | 82,4 | allyl chloride | 45.7 |
| i-butanol | 107,7 | cyclopentadiene | 40 |
| sec-butanol | 99,5 | diethylamine | 56.3 |
| tert-butanol | 82,6 | di-i-propylamine | 84 |
| di-ethylether | 34,6 | formaldehyde | 32 |
| di-n-propyl ether | 90,5 | n-heptane | 98 |

-continued

|  | $t_b$,°C. |  | $t_b$,°C. |
|---|---|---|---|
| di-iso-propyl ether | 67,8 | i-propylamine | 33 |
| tetrahydrofurane | 64,7 | nitrogen dioxide | 21.2 |
| dioxane | 101,3 | triethylamine | 89 |
| acetone | 56,2 | vinyl acetate | 71 |
| methyl ethyl ketone | 79,6 | thiophene | 84 |
| formaldehyde-di-methylacetal | 42,3 | hexene (1) | 63.35 |
|  |  | hexene (2) | 68.1 |
| methyl acetate | 57,1 | hexane (3) | 66.7 |
| ethyl acetate | 77,2 | n-pentane | 36.15 |
| n-propyl acetate | 101,6 | octane | 125.8 |
| i-propyl acetate | 88,8 | isooctane | 99.3 |
| methylene chloride | 40,7 | (2,2,4 trimethylpentane) |  |
| chloroform | 61,3 | furane | 32 |
| carbon tetrachloride | 76,8 | piperidine | 106 |
| ethylenechloride | 84,1 | dilutyl ether | 140 |
| 1,1,1-trichloroethy­lene | 74,1 | ethyl propyl ether | 63.6 |
| isopentan | 27,95 | pentanone | 102 |
| (2-methylbutane) |  | hexanone | 127 |
| isoheptane | 90,0 |  |  |
| (2-methylhexane) |  |  |  |
| isohexane | 60 | formic acid ethyl ester | 54 |
| (2-methylpentane) |  |  |  |
| 3-methylpentane | 63,2 | formic acid allyl ester | 83 |
| 3,3-dimethylpentane | 86,0 |  |  |
| 2,3-dimethylpentane | 89,7 | formamide | 105 |
| 2,4-dimethylpentane | 80,8 |  |  |
| 2,3-dimethylbutane | 58,1 |  |  |
| 2,2-dimethylbutane | 49,7 |  |  |
| 2,2,3-trimethylbutane | 80,9 |  |  |

The examples which follow are provided for purposes of illustration only and to enable those skilled in this art to more clearly understand and practice the present invention, but are not intended to limit the scope of protection of the invention.

EXAMPLE 1

The process of this example is carried out in the apparatus of FIG. 1. For the separation, column I is a distillation column with 34 plates. A mixture of fatty acids with the approximate compositions of 43 weight percent stearic acid and 57 weight percent oleic acid is continuously introduced at the 17th plate of the column as a stream containing benzene as an entrainer, the amount of which is 3.5 times the volume of mixed fatty acids. The system is maintained at a pressure of 145 atm and carbon dioxide is continuously circulated throughout the system. The temperature at the bottom of Column I is 98° C. at the feedplate 95° C. and at the top of the column 92° C. Under these conditions 4 weight percent of fatty acids is dissolved in the vapor phase of the circulating carbon dioxide. The reflux ratio in Column I is 1.5 based on the amount of fatty acids). The distillate withdrawn from the head of Column I and passing to Column II contains 4 weight percent fatty acids (whereof 90 weight percent is stearic acid and 10 weight percent is oleic acid) about 10 weight percent of benzene and 85 weight percent carbon dioxide.

The sump product withdrawn from the bottom of Column I contains 35 weight percent fatty acids (whereof 15 weight percent is stearic acid and 85 weight percent is oleic acid), about 22 weight percent benzene and 43 weight percent carbon dioxide.

In Column II, the bottom temperature is 90° C. and the temperature at the top of the column is 123° C. The reflux in Column II contains about 30 weight percent fatty acids, the composition of which is: 90 weight percent stearic acid and 10 weight percent oleic acid. The material from the bottom of Column II is separated and 60 percent of the total volume is returned to Column I (corresponding to a reflux ratio of 1.5). The remainder is collected as a distillation product. It contains 35 weight percent fatty acids, the composition of which is: 90 weight percent stearic acid and 10 weight percent oleic acid.

EXAMPLE 2

The process of this example is carried out in the apparatus of FIG. 1. For the separation, Column I is a distillation column with 34 plates. A mixture of glycerides of oleic acid with the approximate composition of 8 weight percent glycerol, 63 weight percent monoglyceride, 25 weight percent di-glyceride and 4 weight percent triglyceride is continuously introduced at the 17th plate of the column as a stream containing acetone as an entrainer, the amount of which is 2 times the volume of mixed glycerides. The system is maintained at a pressure of 135 atm and carbon dioxide is continuously circulated throughout the system. The temperature at the bottom of Column I is 70° C., at the feedplate 68° C. and at the top of the column 65° C. Under these conditions, 5.4 weight percent of glycerides is dissolved in the vapor phase of the circulating carbon dioxide. The reflux ratio in Column I is 2 (based on the amount of glycerides). The distillate withdrawn from the head of Column I and passing to Column II contains 5.4 weight percent glycerides (whereof 95 weight percent is monoglyceride and 5 weight percent is glycerol).

The sump product withdrawn from the bottom of Column I contains 37 weight percent glycerides (whereof 5 weight percent is monoglyceride, 80 weight percent is diglyceride and 15 weight percent is triglyceride).

In Column II, the bottom temperature is 65° C. and the temperature at the top of the column is 110° C. The reflux in column II contains about 32 weight percent glycerides, the composition of which is: 95 weight percent monoglyceride and 5 weight percent glycerol. The material from the bottom of Column II is separated and 66 percent of the total volume is returned to Column I (corresponding to a reflux ratio of 2). The remainder is collected as a distillation product. It contains 37 weight percent glycerides, the composition of which is: 95 weight percent monoglycerides and 5 weight percent glycerol.

EXAMPLE 3

The process of this example is carried out in the apparatus of FIG. 1. For the separation, Column I is a distillation column with 34 plates. A mixture of glycerides of stearic acids with the approximate composition of 8 weight percent glycerol, 63 weight percent monoglyceride, 25 weight percent diglyceride and 4 weight percent triglyceride is continuously introduced at the 17th plate of the column as a stream containing acetone as an entrainer, the amount of which is 2 times the volume of mixed glycerides. The system is maintained at a pressure of 145 atm and carbon dioxide is continuously circulated throughout the system. The temperature at the bottom of Column I is 80° C., at the feedplate 78° C. and at the top of the column 75° C. Under these conditions, 5 weight percent of glycerides is dissolved in the vapor phase of the circulating carbon dioxide. The reflux ratio in Column I is 2 (based on the amount of glycerides). The distillate withdrawn from the head of Column I and passing to Column II contains 5.4 weight percent glycerides (whereof 95 weight percent is monoglyceride and 5 weight percent is glycerol).

The sump product withdrawn from the bottom of Column I contains 37 weight percent glycerides (whereof 5 weight percent is monoglyceride, 80 weight percent is diglyceride and 15 weight percent is triglyceride).

In Column II, the bottom temperature is 75° C. and the temperature at the top of the column is 110° C. The reflux in Column II contains about 30 weight percent glycerides, the composition of which is: 95 weight percent monoglyceride and 5 weight percent glycerol. The material from the bottom of Column II is separated and 66 percent of the total volume is returned to Column I (corresponding to a reflux ratio of 2). The remainder is collected as a distillation product. It contains 35 weight percent glycerides, the composition of which is: 95 weight percent monoglycerides and 5 weight percent glycerol.

EXAMPLE 4

The process of this example is carried out in the apparatus of FIG. 1. For the separation, Column I is a distillation column with 34 plates. A mixture of glycerides (palm oil) with free fatty acids with the approximate composition of 83 weight percent triglycerides, 10 weight percent diglycerides, 0.5 weight percent monoglycerides and 7 weight percent free fatty acids is continuously introduced at the 17th plate of the column as a stream containing acetone as an entrainer, the amount of which is 3 times the volume of mixed glycerides. The system is maintained at a pressure of 138 atm and carbon dioxide is continuously circulated throughout the system. The temperature at the bottom of the Column I is 82° C., at the feedplate 79° C. and at the top of the column 75° C. Under these conditions, 3 weight percent of fatty acids and glycerides is dissolved in the vapor-phase of the circulating carbon dioxide. The reflux ratio in Column I is 1.5. The distillate withdrawn from the head of Column I and passing to Column II contains 3 weight percent fatty acids and glycerides (where of 95 weight percent is free fatty acids and 5 weight percent glycerides).

The sump product withdrawn from the bottom of Column I contains 35 weight percent glycerides (whereof 0.1 weight percent is fatty acids and 99.9 weight percent are glycerides).

In Column II, the bottom temperature is 75° C. and the temperature at the top of the column is 110° C. The reflux in Column II contains 30 weight percent fatty acids and glycerides, the composition of which is: 95 weight percent fatty acids and 5 weight percent glycerides. The material from the bottom of Column II is separated and 60 percent of the total volume is returned to Column I. The remainder is collected as a distillation product. It contains 35 weight percent fatty acids and glycerides, the composition of which is: 95 weight percent fatty acids and 5 weight percent glycerides.

EXAMPLE 5

The process of this example is carried out in the apparatus of FIG. 1. For the separation, Column I is a distillation column with 34 plates. Soja oil with the approximate composition of 0.7 weight percent free fatty acids, 1.5 weight percent lecithin and 97.7 weight percent triglycerides is continuously introduced at the 17th plate of the column as a stream containing hexane as an entrainer, the amount of which is 3.5 times the volume of soja oil. The system is maintained at a pressure of 135 atm and carbon dioxide is continuously circulated throughout the system. The temperature at the bottom of Column I is 70° C., at the feedplate 68° C. and at the top of Column I 65° C. Under these conditions, 11 weight percent of triglycerides is dissolved in the vapor phase of the circulating carbon dioxide. The reflux ratio in Column I is 0.2. the distillate withdrawn from the head of Column I and passing to Column II contains 11 weight percent triglycerides, about 1.5 weight percent fatty acids and practically no lecithin.

The sump product withdrawn from the bottom of Column I contains 30 weight percent materials of low volatility, whereof about 30 weight percent is lecithin and 70 weight percent is triglycerides.

In Column II, the bottom temperature is 70° C. and the temperature at the top of the column is 100° C. The reflux in Column II contains 28 weight percent of triglycerides and fatty acids, the composition of which is 98.5 weight percent triglycerides and 1.5 weight percent fatty acids. The material from the bottom of Column II is separated and 17 percent of the total volume is returned to Column I. The remainder is collected as a distillation product. It contains 30 weight percent materials of low volatility, the composition of which is 98.5 weight percent triglycerides and 1.5 weight percent fatty acids.

EXAMPLE 6

The process of this example is carried out in the apparatus of FIG. 1. For the separation, Column I is a distillation column with 34 plates. A mixture of mineral oils with a range of boiling temperatures of from 250° to 400° C. at 18 mm Hg containing very small particles of clay, the removal of which is usually possible by the application of centrifuges only, is continuously introduced at the 17th plate of the column as a stream containing a mixture of low boiling hydrocarbons (boiling temperatures between 50° and 90° C.) as an entrainer, the amount of which is 3.5 times the volume of mixed mineral oils. The system is maintained at a pressure of 100 atm and methane is continuously circulated throughout the system. The temperature at the bottom of Column I is 80° C., at the feedplate 78° C. and at the top of Column I 75° C. Under these conditions, 20 weight percent of mineral oils is dissolved in the vapor phase of the circulating methane. The reflux ratio in Column I is 0.1. The distillate withdrawn from the head of Column I and passing to Column II contains 20 weight percent mineral oils and no clay particles.

The sump product withdrawn from the bottom of Column I contains 35 weight percent mineral oils and clay particles.

In column II the bottom temperature is 75° C. and the temperature at the top of the column is 140° C. The reflux in Column II contains 35 weight percent mineral oils. The material from the bottom of Column II is separated and 10 percent of the total volume is returned to Column I. The remainder is collected as a distillation product. It contains 35 weight percent mineral oils and no clay particles.

EXAMPLE 7

The process of this example is carried out in an apparatus analogous to FIG. 1. For the separation, Column I is a distillation column without plates. A mixture of mineral oils with a range of boiling temperatures of from 150° to 450° C. at 18 mm Hg containing very small particles of clay, the removal of which is usually possible by the application of centrifuges only, is continuously introduced at the top of the column and sprayed to small droplets, which fall down in countercurrent to the supercritical gas stream. The system is maintained at a pressure of 80 atm and toluene which is under supercritical conditions is continuously circulated throughout the system. The temperature at the bottom of Column I is 410° C. and at the top of column I 400° C. The circulating toluene contains as an entrainer diesel oil the amount of which is 2.5 times the volume of the mixture of mineral oils. Under these conditions, 35 weight percent of mineral oils is dissolved in the vapour phase of the circulating toluene. No reflux is used. The distillate withdrawn from the head of Column I and passing to Column II contains 35 weight percent of mineral oils and no clay particles.

In the sump of column I practically dry clay particles collect and are withdrawn from the bottom of Column I.

In Column II the bottom temperature is 400° C. and the temperature at the top of the column is 450° C. The reflux in Column II contains 70 weight percent of mineral oils of low volatility. The material from the bottom of Column II is collected as a distillation product. It contains 70 weight percent mineral oils of low volatility and is free from clay particles.

EXAMPLE 8

The process of this example is carried out in the apparatus of FIG. 1. For the separation, Column I is a distillation column with 34 plates.

Palm oil with the approximate composition of 83 weight percent triglycerides, 10 weight percent diglycerides, 0.5 weight percent monoglycerides, 7 weight percent free fatty acids and 250 ppm carotene is continuously introduced at the 17th plate of the column as a stream containing n-hexane and n-methylpyrrolidone (NMP) [1:1 by volume] as an entrainer, the amount of which is 2 times the volume of mixed glycerides. The system is maintained at a pressure of 70 atm and propane is continuously circulated throughout the system. The temperature at the top of Column I is 105° C., at the feedplate 110° C. and at the bottom of Column II 112° C. Under these conditions, 9 weight percent of fatty acids and glycerides is dissolved in the vapor phase of the circulating propane. The reflux ration in Column I is 0.2. The distillate withdrawn from the head of Column I and passing to Column II contains 9 weight percent fatty acids and glycerides and about 50 ppm carotene. The sump product withdrawn from the bottom of Column I contains 30 weight percent of low volatility, whereof about 3 weight percent is carotene and 97 weight percent glycerides and fatty acids.

In Column II, the bottom temperature is 105° C. and the temperature at the top of the column is 120° C. The reflux ratio in Column II contains 33 weight percent fatty acids and glycerides, the composition of which is 10 weight percent fatty acids and 90 weight percent glycerides. The material from the bottom of Column II is separated and 17 percent of the total volume is returned to Column I. The remainder is collected as a distillation product. It contains 35 weight percent materials of low volatility, the composition of which is 10 weight percent fatty acids and 90 weight percent glycerides.

Throughout this specification, the term "mixture of barely volatile substances" is intended to include mixtures where one of the substances is not volatile at all.

Various modifications may be made in the details of the invention described above and shown in the drawings without departing from the true spirit and scope of the invention.

I claim:

1. A process for substantially separating the components of mixtures of substances at least one of which is of low volatility, while the other is of low or no volatility by using a compressed gas under supercritical conditions, and an entrainer adapted to increase the concentration of said mixtures of substances in the gaseous phase as well as the separation factor between the components to be separated, comprising in combination, feeding such mixture and said entrainer into a first distillation zone, passing said compressed gas upward through said distillation zone, effecting the separation and downward travel of the first component mixed with entrainer, to the bottom of said first distillation zone; passing from the top of said first distillation zone, the compressed gas, entrainer and second component to a point at most as high as the center of a second distillation zone, passing said compressed gas, entrainer and second component upward past a condensing zone at the top of said second distillation zone condensing part of said entrainer so it will travel downward in countercurrent to the compressed gas whereby to substantially free the same from the second component, and to pass to the bottom of said second distillation zone; recycling the compressed gas from the top of the second distillation zone to the bottom of the first distillation zone, recycling part of the bottom product of said second distillation zone to the top of said first distillation zone, whereby to effect substantial separation of said components in the absence of any substantial pressure decrease and the consequent need for recompression.

2. A separation process according to claim 1, wherein the compressed gas used under supercritical conditions, is characterized by the fact that its critical temperature is lower than any temperature prevailing during the separation process.

3. A separation process according to claim 1, wherein the entrainer is characterized by the act that its critical temperature is higher than any temperature prevailing during the separation process, and the further fact that together with gas used under supercritical conditions, it forms a binary system the phase boundary line of which in the pressure-concentration diagram at the working temperatures and pressures prevailing during the separation process, forms a closed loop.

4. A separation process according to claim 1, wherein the substances in the mixtures to be separated include at least one substance of low volatility and another of low or no volatility, said substances preferably being selected from the class consisting of organic and inorganic compounds.

5. A process according to claim 1 in which the entrainer is selected from the group consisting of benzene, toluene, xylene, acetonitrile, acetone, methylene chloride, cyclohexane, hexane, n-heptane, methyl cyclohexane, iso-octane, octane, nonane, decane, furan, 2-methylfuran, furfural, furan-3-aldehyde, ethyl furan or mixtures thereof.

6. A process according to claim 5 in which the entrainer is selected from the group consisting of toluene or xylene at a concentration of from 5 to 70 percent by weight based on the mixture of fatty acids and entrainer.

7. A process according to claim 1 for the substantial separation of saturated and unsaturated fatty acids of low volatility in which the entrainer is furan or a derivative thereof, acetonitrile, acetone, methylene chloride, n-heptane, iso-octane, cyclohexane, methyl cyclohexane, octane, nonane, decane, or mixtures thereof.

8. A process according to claim 1 for the substantial separation of glycerides of low volatility in which the entrainer is an alcohol containing up to four carbon atoms, a ketone containing up to five carbon atoms, or water.

9. A process according to claim 1, for the substantial separation of polyhydric alcohols of low volatility in which the entrainer is an alcohol containing up to four carbon atoms, a ketone containing up to five carbon atoms, or water.

10. A process according to claim 1 in which the supercritical component is selected from the group consisting of aliphatic hydrocarbons, halogen containing aliphatic hydrocarbons containing from 1 to 4 carbon atoms, or carbon dioxide.

11. A process according to claim 1 wherein the compressed gas used under supercritical conditions is ethane, propane, trifluoro-chloromethane, difluoro-dichloromethane, trifluoro-bromomethane, methyl fluoride, ethylene or propylene.

12. A separation process according to claim 1 for substantially separating a mixture of fatty acids essentially consisting of oleic acid and stearic acid, wherein the compressed gas used under supercritical conditions is carbon dioxide, and the entrainer is benzene.

13. A separation process according to claim 1 for substantially separating mono- and diglycerides, wherein the compressed gas used under supercritical conditions is carbon dioxide, and the entrainer is acetone.

14. A separation process according to claim 1 for substantially separating a mixture of glycerides and free fatty acids, wherein the compressed gas used under supercritical conditions is carbon dioxide, and the entrainer is acetone.

15. A separation process according to claim 1 for substantially separating triglycerides and lecithin contained in soja oil, wherein the compressed gas used under supercritical conditions is carbon dioxide, and the entrainer is hexane.

16. A separation process according to claim 1 for substantially separating a mixture of mineral oils of low volatlity and very small particles of clay, wherein the compressed gas used under supercritical conditions is methane, and the entrainer is a mixture of hydrocarbons with boiling temperatures between 50° and 90° C.

* * * * *